US012788475B2

(12) United States Patent
Liu et al.

(10) Patent No.: US 12,788,475 B2
(45) Date of Patent: Nov. 10, 2026

(54) ABLATION DEVICE

(71) Applicant: HANGZHOU DINOVA EP TECHNOLOGY CO., LTD., Hangzhou (CN)

(72) Inventors: Cheng Liu, Hangzhou (CN); Kun Wang, Hangzhou (CN)

(73) Assignee: HANGZHOU DINOVA EP TECHNOLOGY CO., LTD., Hangzhou (CN)

( * ) Notice: Subject to any disclaimer, the term of this patent is extended or adjusted under 35 U.S.C. 154(b) by 176 days.

(21) Appl. No.: 18/730,960

(22) PCT Filed: Dec. 16, 2022

(86) PCT No.: PCT/CN2022/139652
§ 371 (c)(1),
(2) Date: Jul. 22, 2024

(87) PCT Pub. No.: WO2023/138275
PCT Pub. Date: Jul. 27, 2023

(65) Prior Publication Data

US 2025/0099161 A1 Mar. 27, 2025

(30) Foreign Application Priority Data

Jan. 21, 2022 (CN) ......................... 202210077700.5

(51) Int. Cl.
*A61B 18/14* (2006.01)
*A61B 18/00* (2006.01)

(52) U.S. Cl.
CPC .... *A61B 18/14* (2013.01); *A61B 2018/00077* (2013.01); *A61B 2018/0016* (2013.01);
(Continued)

(58) Field of Classification Search
CPC ..... A61B 18/12; A61B 18/14; A61B 18/1492; A61B 2018/00077; A61B 2018/0016;
(Continued)

(56) References Cited

U.S. PATENT DOCUMENTS 5,293,869 A * 3/1994 Edwards .............. A61B 5/6853 600/375
5,722,401 A * 3/1998 Pietroski .............. A61B 5/6858 600/374
(Continued)

FOREIGN PATENT DOCUMENTS

CN 213525440 U 6/2021
CN 113440243 A 9/2021
(Continued)

OTHER PUBLICATIONS

WIPO, International Search Report and Written Opinion for International Application No. PCT/CN2022/139652, Mar. 3, 2023.

*Primary Examiner* — Khadijeh A Vahdat
(74) *Attorney, Agent, or Firm* — HAUPTMAN HAM, LLP

(57) ABSTRACT

An ablation device includes an outer tube; an ablation assembly, provided at a distal end of the outer tube and including a radially collapsible and expandable support frame and a plurality of electrodes arranged on the support frame, wherein at least one first electrode used for mapping is included in the plurality of electrodes; and a connector, provided at a proximal end of the outer tube, the connector including a plurality of conductive terminals, the connector being electrically connected to the plurality of electrodes through the plurality of conductive terminals, the plurality of conductive terminals including at least one first terminal, and each first terminal being electrically connected to one corresponding first electrode in a one-to-one correspondence
(Continued)

mode, so that when the connector is connected to an external mapping device, the first electrode implements mapping through the first terminal.

19 Claims, 11 Drawing Sheets

(52) U.S. Cl.
CPC ............... *A61B 2018/00178* (2013.01); *A61B 2018/00184* (2013.01); *A61B 2018/00267* (2013.01); *A61B 2018/00577* (2013.01); *A61B 2018/00839* (2013.01); *A61B 2018/1467* (2013.01)

(58) Field of Classification Search
CPC A61B 2018/00178; A61B 2018/00184; A61B 2018/00214; A61B 2018/00267; A61B 2018/00279; A61B 2018/00351; A61B 2018/00357; A61B 2018/00577; A61B 2018/00839; A61B 2018/1405; A61B 2018/1467; A61B 2018/1475
See application file for complete search history.

(56) References Cited

U.S. PATENT DOCUMENTS

| | | | | |
|---|---|---|---|---|
| 2004/0019349 | A1 | 1/2004 | Fuimaono et al. | |
| 2014/0257069 | A1 * | 9/2014 | Eliason ................ | A61B 5/6858 600/373 |
| 2014/0276712 | A1 * | 9/2014 | Mallin ............... | A61B 18/1492 606/33 |
| 2016/0331459 | A1 * | 11/2016 | Townley ................ | A61N 5/022 |
| 2021/0161582 | A1 * | 6/2021 | Byrd .................. | A61B 18/1206 |
| 2024/0215854 | A1 * | 7/2024 | Rodriguez Soto ..... | A61B 5/062 |

FOREIGN PATENT DOCUMENTS

| | | | | |
|---|---|---|---|---|
| CN | 113939241 A | | 1/2022 | |
| WO | WO-2021126980 A1 | * | 6/2021 | ......... A61B 18/1492 |

* cited by examiner

ABLATION DEVICE

The present application is a National Stage of International Application No. PCT/CN2022/139652, filed Dec. 16, 2022, which claims priority to Chinese Patent Application No. 202210077700.5 (entitled "Ablation Device") filed with China National Intellectual Property Administration on Jan. 21, 2022, which are incorporated herein by reference in their entirety.

TECHNICAL FIELD

The present invention relates to the technical field of medical devices, and particularly to an ablation device.

BACKGROUND

Electrophysiological mapping plays a very important role in the field of electrophysiology, which is used to record electrophysiological signals in vivo, so as to find abnormal lesions and guide ablation accordingly. After ablation treatment, the effect of treatment is then verified by mapping.

The traditional electrophysiological mapping is generally implemented by using a mapping catheter and the ablation therapy is implemented by using an ablation catheter. This leads to the need to insert and retract multiple devices in and from the patient's body during the operation. For example, during the procedure, a mapping catheter is used for electrophysiological mapping. Once the mapping is completed, the mapping catheter can be removed, an ablation catheter will be then inserted in situ. After the ablation, the mapping catheter is inserted again for mapping, to verify the effect of the ablation treatment. However, it needs to introduce both ablation catheter and the mapping catheter during the procedure which causes many defects such as complicated operation steps, long operation time and high cost.

SUMMARY

To solve the above problems, the present invention provides an ablation device, which includes an outer tube; an ablation assembly, provided at a distal end of the outer tube and including a radially collapsible and expandable support frame and a plurality of electrodes arranged on the support frame, wherein the plurality of electrodes includes at least one first electrode for mapping; and a connector, provided at a proximal end of the outer tube, wherein the connector includes a plurality of conductive terminals, the connector is electrically connected to the plurality of electrodes by means of the plurality of conductive terminals, the plurality of conductive terminals (32) includes at least one first terminal, and each of the at least one first terminal is electrically connected to one corresponding first electrode in a one-to-one correspondence mode, so that when the connector is connected to an external mapping device, the first electrode implements mapping by means of the first terminal.

According to the ablation device provided in the embodiments of the present invention, a target ablation area can be ablated by means of the radially expandable support frame and the plurality of electrodes arranged on the support frame. Moreover, the first electrode(s) of the electrodes is/are connected to the first terminal(s) on the connector in a one-to-one correspondence mode. Therefore, when the connector is connected to an external mapping device, the first electrode can also be used for electrophysiological mapping by the corresponding first terminal. In this way, the ablation device has the functions of both mapping and ablation, making the surgical operations more convenient, and improving the operation efficiency.

LIST OF REFERENCE NUMERALS

Figure 1A:
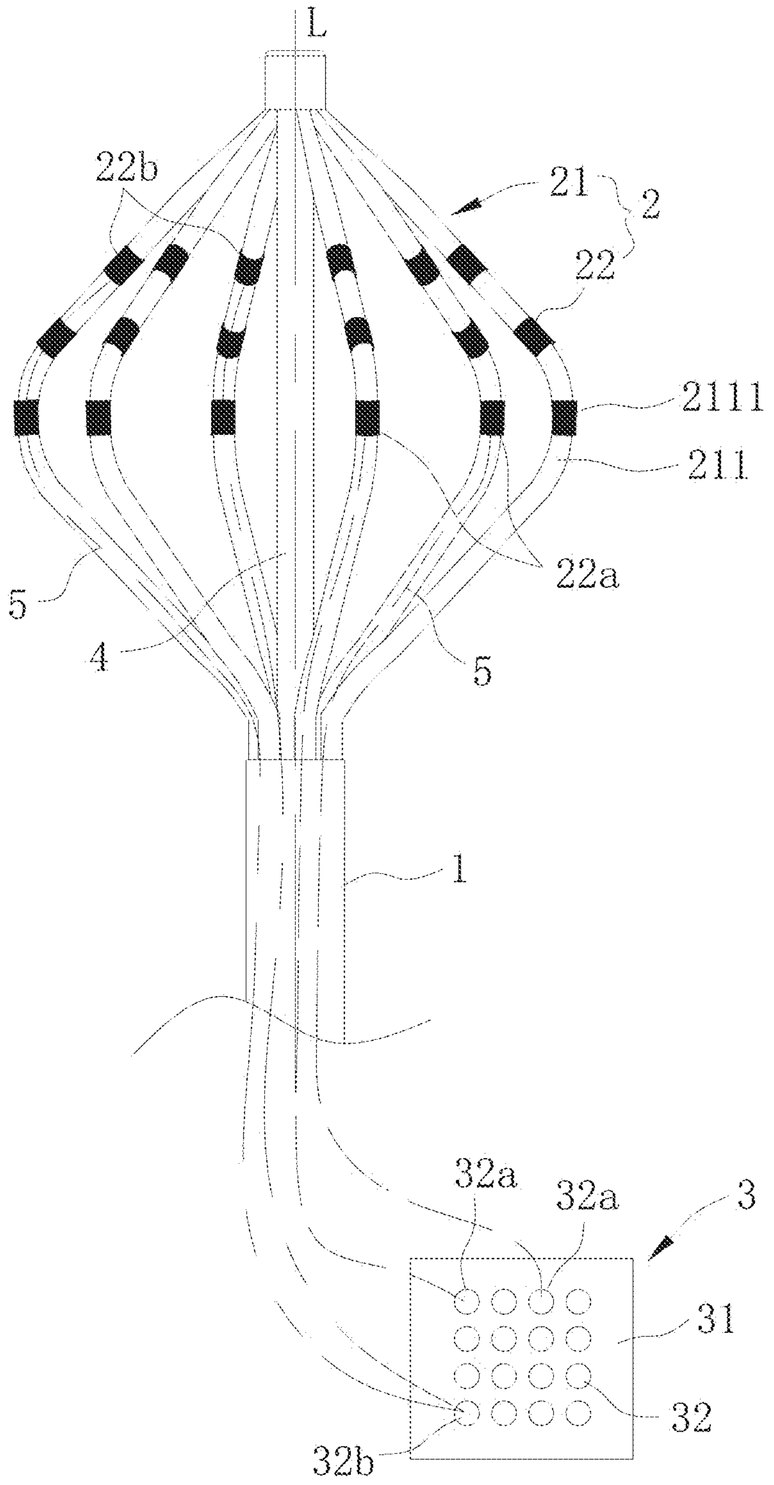
FIG. 1 is a schematic view of an ablation device according to a first embodiment of the present invention.
FIG. 1*b* is a schematic view of a connector mounted on a handle.
FIG. 1*c* is a schematic view of a connector connected to an external ablation energy source or an external mapping device.
FIG. 1*d* is a schematic view of a driving member of an ablation device that is provided with a reference electrode.
FIG. 1*e* is a schematic view of a support frame of an ablation device that is provided with a reference electrode at a distal end.

- 1. outer tube;
- 100. handle;
- 200. external ablation energy source;
- 300. external mapping device;
- 2. ablation assembly; 21. support frame; 211. bearing rod; 2111. outermost end;
- 2113. backward enclosure portion; 213. locating frame; 2131. main rod; 2132. branch rod; 215. support rod; 22. electrode; 22*a*. first electrode; 22*b*. second electrode;
- 3. connector; 31. insulating housing; 32. conductive terminal; 32*a*. first terminal; 32*b*. second terminal;
- 4. driving member; 41. insertion hole; 43. driving rod; 44. joint;
- 5. wire;
- 6. reference electrode.

DESCRIPTION OF EMBODIMENTS

Typical embodiments embodying the characteristics and advantages of the present invention will be described in detail hereinafter. It should be understood that various variations of the present invention can be made in various embodiments, without departing from the scope of the present invention. The description and accompanying drawings herein are provided essentially for illustration, instead of limiting the present invention.

In the description of the present application, it should be understood that directions or location relationships indicated by the terms "center", "longitudinal", "transverse", "length", "width", "thickness", "upper", "lower", "front", "rear", "left", "right", "vertical", "horizontal", "top", "bottom", "inner", "outer", "clockwise", and "counterclockwise" are directions or location relationships shown based on the accompanying drawings, which are merely provided for the purpose of describing the present application and simplifying the description, but are not used to indicate or imply that a device or an element must have a particular direction, or must be constructed and operated in a particular direction. Therefore, they cannot be construed as limiting on the present application. Furthermore, the terms "first", and "second" are used merely for the purpose of description, and shall not be construed as indicating or implying relative importance or implying a quantity of indicated technical features Therefore, a feature restricted by "first" or "second" may explicitly or implicitly include one or more of the features. In the description of the present application, "a plurality of" means two or more, unless explicitly specified.

An embodiment of the present invention provides an ablation device having mapping function, which can be used for cardiac ablation, by delivering the ablation device to a specific position of the heart by percutaneous puncture and ablating the pulmonary vein, the left atrial appendage, or trigger foci (such as superior vena cava and coronary sinuatrial orifice) of non-pulmonary vein origins combined with typical atrial flutter by using an external ablation energy source such as pulsed electric field, radio frequency or microwave, so as to achieve the effect of electrical isolation. It can be understood that cardiac ablation is a typical application of the ablation device, and if feasible, the ablation device can also be applied to other tissues, which is not limited herein.

The ablation device is provided with an electrode for ablation, which can also be directly used for electrophysiological mapping before and after ablation. In this way, the ablation device has the functions of mapping and ablation at the same time, making the surgical operations more convenient, and improving the success rate of surgery.

To facilitate the understanding of the technical solutions of the present invention, the present invention will be described in detail in connection with several embodiments. It is to be understood that where there are no contradictions, features in various embodiments of the present invention can be combined with each other without conflict.

For ease of description, the definitions of some terms involved herein are interpreted as follows:

Proximal and distal ends: In the field of interventional medical devices, the end of a medical device inserted into the human or animal body that is close to an operator is called "proximal" end, and the end far away from the operator is called "distal" end. The "proximal end" and "distal end" of any components in the ablation device are defined herein according to this rule. "Axial direction" generally refers to a length direction of a medical device when it is delivered, "radial direction" generally refers to a direction of the medical device that is perpendicular to its "axial direction", and "circumferential direction" generally refers to a direction around the "axial direction". The "axial direction", "radial direction" and "circumferential direction" of relevant components in the ablation device are defined herein according to this rule. These definitions are merely provided for convenience of expression and do not constitute a limitation on the present application. If there are any exceptions, a reasonable explanation can be made by combining the attached drawings and the common understanding of the terms by those skilled in the art.

Insulating layer: It is formed by insulating a surface of a component, and is used to insulate this portion of the component. Particularly, the insulating layer is formed by coating, at a position intended to be insulated, an insulating coating material, including, but not limited to, a Parylene coating, a poly-tetra-fluoroethylene (PTFE) coating, and a polyimide (PI) coating; or by applying, at a position intended to be insulated, an insulating film, including, but not limited to, fluorinated-ethylene-propylene (FEP), polyurethane (PU), ethylene-tetra-fluoro-ethylene (ETFE), polyfluoroalkoxy (PFA), PTFE, poly-ether-ether-ketone (PEEK), and silica gel; or by arranging an insulating sleeve tube around at a position intended to be insulated, wherein the material of the insulating sleeve tube includes, but is not limited to, FEP, PU, ETFE, PFA, PTFE, PEEK, and silica gel.

Pulsed-field ablation: Irreversible electric breakdown, also known as irreversible electroporation (IRE) in the medical field, of cell membrane is caused by a high-intensity pulsed electric field, to induce cell apoptosis, so that non-thermal ablation of cells is realized without the use of heat sink effect. A high-voltage pulse sequence generates less heat and does not require the cooling with physiological saline, effectively reducing the occurrence of steam pops, eschar and thrombosis. The duration of pulsed-field ablation is short. The time of treatment by applying a group of pulse sequences is less than 1 minute, and the whole ablation time is generally less than 5 minutes. Moreover, because different tissues have different response thresholds to pulsed electric field, it is possible to ablate the myocardium without interfering with other adjacent tissues, thus avoiding accidental injury to adjacent tissues. In addition, compared with other forms of energy, pulsed-field ablation does not require heat conduction to ablate the deep tissue, because all myocardial cells distributed within a certain electric field intensity will be electroporated, reducing the requirement for contact pressure of a catheter during the ablation. Therefore, even if the ablation device is not completely attached to an inner wall of a tissue, the ablation effect of IRE will not be affected.

FIRST EMBODIMENT

Figure 1B:
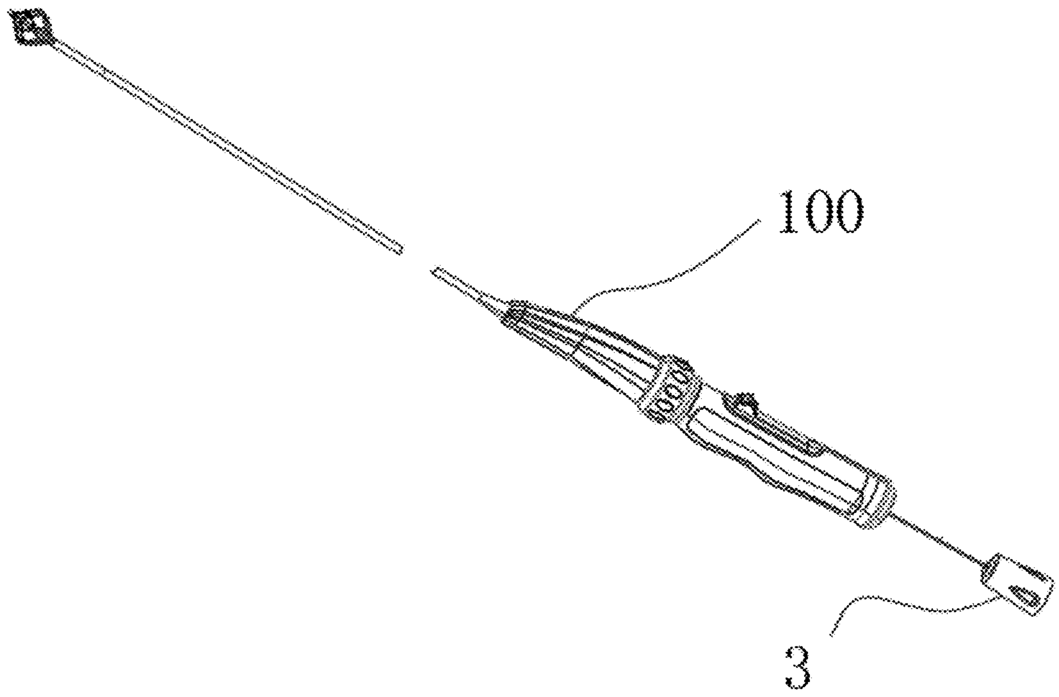

Referring to FIG. 1*a*, an ablation device according to this embodiment mainly includes an outer tube 1, an ablation assembly 2 provided at a distal end of the outer tube 1, and a connector 3 provided at a proximal end of the outer tube 1. In this embodiment, the ablation device further includes a driving member 4 inserted in the outer tube 1 and connected to the ablation assembly 2. The ablation device can be delivered to the interior of the heart by a delivery device that generally includes a sheath, and a handle, etc. For the specific structure of the delivery device, reference can be made to related technologies in the art. The connector 3 of the ablation device can be arranged on a handle 100, as shown in FIG. 1*b*.

Referring to FIG. 1*a* again, the outer tube 1 has a hollow tubular structure, with an axis extending in a distal-proximal direction. The outer tube 1 has a single axial lumen or a central lumen (not shown) therein. According to requirement in practice, the outer tube 1 can also be constructed to have a plurality of lumens, to accommodate, a pull wire, a lead wire, a sensor cable, and any other wires, cables and/or tubes and structures that may be needed in a specific application therein.

It can be understood that the outer tube 1 can also be of any suitable configuration, and made of any suitable material. For example, one configuration includes an outer wall made of a polymer material such as polyurethane or polyether-block-amide (PEBAX). The outer tube 1 has certain flexibility and can be bent to adapt to the bending structure inside the heart.

The ablation assembly 2 includes a radially collapsible and expandable support frame 21 and a plurality of electrodes 22 arranged on the support frame 21.

A proximal end of the support frame 21 is connected to the distal end of the outer tube 1, and a distal end of the support frame 21 is gathered towards the axis L of the outer tube 1. In this embodiment, the distal end of the support frame 21 is converged at the distal end of the driving member 4. FIG. 1*a* schematically shows a structure in which the support frame 21 is in an expanded state. In this case, the two ends of the support frame 21 are converged and the intermediate portion is expanded, and the contour of the support frame 21 is substantially in the shape of a mesh basket. The support frame 21 may also have other configurations, such as spherical, egg-shaped, pumpkin-shaped, lantern-shaped, and oval-shaped configurations etc.

On the basis of the structure shown in FIG. 1*a*, the support frame 21 can be radially inwardly collapsed relative to the axis L of the outer tube 1, that is, the intermediate portion of the support frame 21 can also be gathered towards the axis L of the outer tube 1. The support frame 21 will be straightened to have a substantially linear shape in a collapsed state. The axial length of the support frame 21 in the collapsed state will be greater than that in the expanded state.

In the collapsed state, the support frame 21 can be received in a sheath, for convenient delivery to the human body through the sheath. After delivery to a target ablation site through the sheath, the support frame 21 is released from the sheath, and then radially expanded to the expanded state shown in FIG. 1*a*.

The radial expansion of the support frame 21 may be self-expansion and unfolded when it extends out of the sheath, or the support frame 21 may expand radially by human manipulation or intervention after it extends out of the sheath. For example, in this embodiment, the driving member 4 can be used to control the collapse and expansion of the support frame 21, which will be described in detail below.

The support frame 21 can be prepared by cutting a pipe made of an elastic metal or by weaving an elastic metal wire, or processed by combining local weaving with local pipe cutting, wherein the parts obtained by different processing methods can be welded or fixed to each other by coupling elements. The pipe may be made of a metal or nonmetal material, preferably a memory metal material or a nickel-titanium alloy material. In this embodiment, the support frame 21 can be cut and shaped from a nickel-titanium alloy pipe.

Particularly, the support frame 21 includes a plurality of bearing rods 211 arranged circumferentially around the axis L of the outer tube 1. The plurality of bearing rods 211 define a radially collapsible and expandable structure. In this embodiment, six bearing rods 211 are arranged circumferentially around the axis L of the outer tube 1, and the bearing rods 211 are uniformly arranged in the circumferential direction. In other embodiments, four, five, six, seven, eight, nine, ten, eleven, twelve or any other suitable number of bearing rods 211 can be provided. The bearing rods 211 may be evenly or unevenly distributed at intervals in the circumferential direction.

A proximal end of each bearing rod 211 is connected to the distal end of the outer tube 1, and distal ends of the plurality of bearing rods 211 are gathered towards the axis L of the outer tube 1. In this embodiment, the distal end of each bearing rod 211 is connected onto the driving member 4, and the support frame 21 can be collapsed or expanded under the control of the driving member 4.

The driving member 4 is coaxially arranged in the outer tube 1. A distal end of the driving member 4 extends distally out of the distal end of the outer tube 1 and is connected to the distal end of each bearing rod 211. The driving member 4 can move axially relative to the outer tube 1, to drive the support frame 21 to expand or contract in the radial direction.

A proximal end of the driving member 4 can be connected to the handle 100, and the handle 100 pulls the driving member 4 to drive the driving member 4 to move in the axial direction. When the driving member 4 moves relative to the outer tube 1 in a distal-to-proximal direction, the distal end of each bearing rod 211 moves proximally with the driving member 4, and the intermediate portion of the bearing rod 211 will gradually swell outward in the radial direction. As a result, the outer diameter of the support frame 21 will increase, that is, the support frame 21 expand outwards. On the contrary, when the driving member 4 moves relative to the outer tube 1 in a proximal-to-distal direction, the distal end of each bearing rod 211 moves distally with the driving member 4, the bearing rod 211 is straightened, and the intermediate portion of the bearing rod 211 is gradually drawn close to the axis L of the outer tube 1 in the radial direction. As a result, the outer diameter of the support frame 21 will decrease. Therefore, the outer diameter of the support frame 21 can be flexibly adjusted by the driving member 4, so that the support frame 21 can adapt to blood vessels (such as pulmonary veins) or other tissues with different diameters, and a target ablation area can be ablated with any appropriate outer diameter, instead of ablation with the restriction that the support frame 21 needs to have the maximum axial compression (that is, the maximum radial expansion). This improves the adaptability of the support frame 21 to the anatomical shapes of different target ablation areas, and facilitates the operation of the ablation device, so as to achieve a good ablation effect.

The driving member 4 can be a steel cable, a flexible polyimide (PI) pipe, a fluorinated polyethylene (PDFE) pipe, a stainless steel pipe, or a pipe made of other polymer materials. When the driving member 4 has a tubular structure, the driving member 4 has a certain structural strength, to buffer the external force on the bearing rod 211, and effectively ensure the position stability of the bearing rod 211.

In some embodiments, the ablation device may not be provided with the driving member 4, and the support frame 21 expands in the radial direction by self-expansion. In this case, the diameter of the support frame 21 is not adjustable, and it is applicable to a target ablation area with a fixed size.

A plurality of electrodes 22 are arranged on each bearing rod 211 of the support frame 21. After the support frame 21 expands radially, each bearing rod 211 can be attached to an inner wall of a tissue inside the heart, and the tissue is ablated by the electrode 22 using ablation energy. It should be noted that the electrodes 22 are arranged on the support frame 21, and during the radial expansion of the support frame 21, the radial positions of the electrodes 22 may change with the expansion of the support frame 21.

In this embodiment, each bearing rod 211 is provided with a plurality of electrodes 22 at intervals in the axial direction. For the plurality of bearing rods 211, the electrodes 22 correspond one-to-one in the axial direction and are arranged at intervals in the circumferential direction around the axis L of the outer tube 1. In other embodiments, one or more electrodes 22 may be provided only on some of the bearing rods 211.

As an example, three electrodes 22 are provided on each bearing rod 211 in this embodiment. It can be understood that the number of electrodes 22 can also be set reasonably according to actual needs. The position of the bearing rod 211 farthest from the axis L of the outer tube 1 in the radial direction is called the outermost end 2111. In this embodiment, each electrode 22 is arranged between the distal end and the outermost end 2111 of the bearing rod 211, so that the distance between the electrodes 22 can be ensured to be in a relatively suitable range to avoid arcing, and the electrodes 22 can be ensured to well conform to the atrial tissue and maintain good attachment. One of the electrodes 22 is located at the outermost end 2111.

The electrode 22 may be a ring electrode, a sheet electrode, a punctiform electrode or a spherical electrode, which is not particularly limited in this embodiment. The electrode 22 can be made of a platinum-iridium alloy, gold, other platinum alloys, stainless steel, nickel-titanium or any other biocompatible medical metals.

The inner wall of each electrode 22 is welded with a wire 5 having an insulating layer. The bearing rod 211 includes a rod body and an insulating sleeve tube arranged around the rod body. The insulating sleeve tube is made of PEBAX tube or other polymer insulating materials, which ensures the insulation between the electrode 22 and the rod body. One, two or more layers of the insulating sleeve tube can be provided, which is not limited herein. The cross-sectional shape of the rod body can be oval, circular, rectangular, semi-circular, round drum or other shapes, which is not limited herein. In this embodiment, the rod body is made of a NiTi wire, so that the rod body has excellent elasticity and strength and can be well attached to the target ablation area. It is to be understood that the rod body can also be made of other materials, such as stainless steel or polymer materials.

The electrode 22 is arranged around on the insulating sleeve tube of the bearing rod 211, to ensure the insulation between the electrode 22 and the rod body. The wire 5 is positioned between the rod body and the insulating sleeve tube. That is, the inner surface of each electrode 22 is connected to the connector 3 by the wire 5 extending through the surface of the insulating sleeve tube and along the bearing rod 211 and the outer tube 1. The electrode 22 and the wire 5 are connected by welding or other special processes.

The connector 3 generally includes an insulating housing 31 and a plurality of conductive terminals 32 disposed on the insulating housing 31. The connector 3 can be mounted on the handle 100 through the insulating housing 31. The plurality of conductive terminals 32 can be arranged according to the actual needs, and are not limited to the arrangement shown in FIG. 1*a*. The structure of the conductive terminal 32 is not limited, and may be a solid needle terminal, or pogo pin, etc.

Figure 1C:
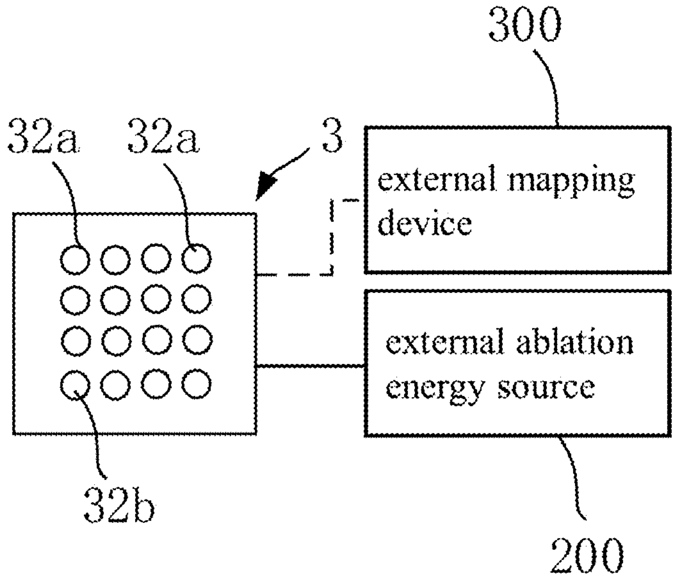

The plurality of conductive terminals 32 are electrically connected to the plurality of electrodes 22 of the ablation assembly 2 through the wires 5, and the wire 5 and the conductive terminal 32 can be connected by welding. By means of the conductive terminals 32, the connector 3 can be optionally connected to an external ablation energy source 200 (as shown in FIG. 1*c*) or an external mapping device 300 (as shown in FIG. 1*c*). When the connector 3 is connected to the external ablation energy source 200, the ablation energy can be transmitted to the electrode 22 through the conductive terminal 32 and the wire 5, whereby the electrode 22 can be used for ablation. When the connector 3 is connected to the external mapping device, the electrode 22 meeting the mapping requirements can transmit the collected electrophysiological signals to the outside through the wire 5 and the conductive terminal 32.

The complete connection relationship between the plurality of conductive terminals 32 and the plurality of electrodes 22 is not shown in FIG. 1*a*. Depending on the different functions of the electrode 22, the conductive terminal 32 and the electrode 22 may have correspondingly different connection relationships. For example, at least one first electrode 22*a* is included in the plurality of electrodes 22 of the ablation assembly 2, wherein the first electrode 22*a* can be used for mapping. The first electrode 22*a* is used for ablation when ablation is needed, and for mapping before and after ablation. FIG. 1*a* exemplarily shows two first electrodes 22*a*, and the two first electrodes 22*a* are arranged on two respective bearing rods 211. Corresponding to the two first electrodes 22*a*, two first terminals 32*a* are included in the plurality of conductive terminals 32 of the connector 3, and each first terminal 32*a* is electrically connected to a corresponding first electrode 22*a* in a one-to-one correspondence mode. That is, one first terminal 32*a* is only connected to one first electrode 22*a* through a corresponding wire 5, and the one first terminal 32*a* will not be connected to other electrodes 22. In this case, after the electrophysiological signal collected by each first electrode 22*a* is transmitted through the first terminal 32*a*, it can clearly and uniquely reflect the electrophysiological state at a specific position in the human body, that is, the position where the first electrode 22*a* is located. Therefore, electrophysiological mapping can be accurately carried out, and the first electrode 22*a* can be used for mapping through the corresponding first terminal 32*a*. The number and arrangement of the first electrodes 22*a* can be varied, and are not limited to the two shown in FIG. 1*a*.

Furthermore, because the first electrode 22*a* and the first terminal 32*a* are electrically connected in a one-to-one correspondence manner, when the connector 3 is connected to the external ablation energy source 200 (as shown in FIG. 1*c*), the first terminal 32*a* can be independently controlled to power on or off the corresponding first electrode 22*a*. The area where the first electrode 22*a* is located can be locally ablated when the first electrode 22*a* is powered on, with no need to ablate the whole target ablation area. Therefore, the ablation device can realize regional ablation. It is possible to avoid the injury of the tissue that is not intended to be ablated by regional local ablation. Ablation energy can directionally act on the tissue intended to be ablated, thus increasing the utilization rate of ablation energy, reducing the dissipation of ablation energy in blood, and reducing unwanted bubbles generated in electrolysis of blood. During the regional ablation, not all the electrodes 22 need to be electrified, so as to reduce the total current during ablation, alleviate possible stimulation to the body, reduce short circuit or arcing caused by too many electrodes 22, and improve the safety.

In some embodiments of the present disclosure, when the connector 3 is connected to the external ablation energy source 200, the first electrode 22*a* can be independently controlled by the first terminal 32*a* to discharge, so that the first electrode 22*a* controlled to discharge can transfer the ablation energy outputted by the external ablation energy source 200 to the area where the first electrode 22*a* is located for local ablation.

In this embodiment, the plurality of electrodes 22 of the ablation assembly 2 also include a plurality of second electrodes 22*b* for ablation only. FIG. 1*a* exemplarily shows two second electrodes 22*b*, and the two second electrodes 22*b* are arranged on two respective bearing rods 211. One second terminal 32*b* electrically connected to the two second electrodes 22*b* is included in the plurality of conductive terminals 32 of the connector 3. That is, the two second electrodes 22*b* are connected to this second terminal 32*b* through their respective wires 5. Therefore, the two second electrodes 22*b* connected to the second terminal 32*b* will have the same polarity during ablation.

The number of the second electrode 22*b* is not limited to two as shown in FIG. 1*a*, and more second electrodes 22*b* can be provided. The number of the second terminal 32*b* is less than or equal to that of the second electrode 22*b*. When the number of the second terminal 32*b* is less than that of the second electrode 22*b*, the plurality of second electrodes 22*b* can be electrically connected to the same second terminal 32*b* in a mode of connection as shown in FIG. 1*a*, so as to reduce the number of the second terminal 32*b*. When the number of the second terminal 32*b* is equal to that of the second electrode 22*b*, the second terminals 32*b* can be used to endow the respective second electrodes 22*b* with different polarities as required, which is beneficial to the formation of different electric field distributions to meet different ablation requirements. In this case, the second terminals 32*b* can actually be connected to the second electrodes 22*b* in a one-to-one correspondence mode, and regional ablation can also be achieved in this instance.

It is to be noted that the above description of the connection relationship between the electrode 22 and the conductive terminal 32 with reference to FIG. 1*a* is merely a schematic illustration of the principle. In practical connection, a reasonable connection relationship can be formed between the electrode 22 and the conductive terminal 32 according to the function of the electrode 22, and the corresponding function of the electrode 22 can be realized with the aid of the conductive terminal 32.

When the electrode 22 is used for ablation, the connector 3 transfers the ablation energy of the connected external ablation energy source 200 to the electrode 22 via the conductive terminal 32, and then the electrode 22 ablates the target ablation area. In this embodiment, all electrodes 22 including the first electrode 22*a* and the second electrode 22*b* can be used for ablation.

Taking the external ablation energy source 200 being of pulsed energy as an example, the voltage range of the pulse signal received by the electrode 22 is in the range of 500V to 3000V, including all values and subranges therebetween; and the pulse frequency is in the range of 500 Hz to 500 kHz, including all values and subranges therebetween. The pulse energy can be a unipolar high-voltage pulse power supply or a bipolar high-voltage pulse power supply. The waveform of a bipolar high-voltage pulse signal has alternating pulses of positive and negative polarity in each period. The maximum voltage that the wire 5 bears is 3000 V. All the electrodes 22 can be divided into one or more positive-negative electrode sets. In some embodiments, a plurality of electrodes 22 on each bearing rod 211 can be arranged to have the same polarity that is opposite to the polarity of the electrodes 22 on adjacent carrier rods 211. In some other embodiments, the polarities of two adjacent electrodes 22 on each bearing rod 211 are opposite, and the polarities of the axially corresponding electrodes 22 on adjacent bearing rods 211 are opposite; or the polarities of two adjacent electrodes 22 on each bearing rod 211 are opposite, and the polarities of the axially corresponding electrodes 22 on adjacent bearing rods 211 are the same. The energy pulse received by the electrode 22 include single-phase pulses or biphasic pulses, and each electrode 22 can be configured to have single-phase or biphasic pulses with different parameters such as voltage, pulse width, repetition frequency, duty ratio and pulse number.

When the electrode 22 is used for mapping, the connector 3 is connected to the external mapping device 300. In this case, only the first electrode is used for mapping. The electrophysiological signal of the target ablation area is collected by the first electrode 22*a* and then transmitted to the external mapping device 300 through the first terminal 32*a*.

The first electrode 22*a* can be arranged and used for mapping through many methods, which are described below. For case of description, this embodiment is described by way of example in which three electrodes 22 are provided on each bearing rod 211. The three electrodes 22 on each bearing rod 211 are called electrode 22 #1, electrode 22 #2, and electrode 22 #3 in sequence from the distal end to the proximal end, wherein the electrode 22 #3 is located at the outermost end 2111 of the bearing rod 211.

First method: One first electrode 22*a* is provided on at least two respective bearing rods 211.

In this method, when the connector 3 is connected to the external mapping device, any two of the first electrodes 22*a* are used as a mapping electrode pair for mapping.

Any electrode 22 on the bearing rod 211 can be used as the first electrode 22*a*, and the axially corresponding electrodes 22 on different bearing rods 211 can be used as the first electrodes 22*a*. That is, the electrodes 22 #1 on the bearing rods 211 are used as the first electrodes 22*a*, the electrodes 22 #2 on the bearing rods 211 are as the first electrodes 22*a*, or the electrodes 22 #3 on the bearing rods 211 are as the first electrodes 22*a*. In addition, the electrodes 22 on two bearing rods 211 that are not corresponding to each other in the axial direction may be used as the first electrodes 22*a*. For example, the electrode 22 #1 on one bearing rod 211 is used as the first electrode 22*a*, and the electrode 22 #3 on another bearing rod 211 is used as the first electrode 22*a*.

Preferably, all the bearing rods 211 are respectively provided with one first electrode 22*a*, so more choices are feasible. Moreover, as the number of the first electrode 22*a* increases, the scope and efficiency of collection of the electrophysiological signals are improved, making the mapping more accurate.

Taking one first electrode 22*a* being provided on each bearing rod 211 as an example. During mapping, the first electrodes 22*a* on two adjacent bearing rods 211 form a mapping electrode pair for electrophysiological mapping. For example, two adjacent electrode 22 #3 form a mapping electrode pair. Definitely, any two first electrodes 22*a* may also be used as a mapping electrode pair. For example, any two electrodes 22 #3 are used as the first electrodes 22*a* and form a mapping electrode pair.

Particularly, it is to be noted that the electrode 22 #3 on each bearing rod 211 is preferably used as the first electrode 22*a*. Compared with the case where the electrode 22 #1 or the electrode 22 #2 is used as the first electrode 22*a*, because the electrode 22 #3 is located at a position on the bearing rod 211 that is farthest from the axis L of the outer tube 1 in the radial direction, that is, a position where the support frame 21 has the largest radial dimension after expansion, the electrode 22 #3 can be full attached to the target ablation area after the support frame 21 is expanded, so the attachment is good and the potential can be mapped more easily.

Second method: Two non-adjacent first electrodes 22*a* are included in a plurality of electrodes 22 arranged on at least one bearing rod 211.

In this method, when the connector 3 is connected to the external mapping device, any two first electrodes 22*a* form a mapping electrode pair for mapping. It is preferable that two first electrodes 22*a* on the same bearing rod 211 are used as a mapping electrode pair. However, in other embodiments, two first electrodes 22*a* on different bearing rods 211 may be used as a mapping electrode pair.

Corresponding to the method of arrangement of the electrode 22 in this embodiment, the electrode 22 #1 and the electrode 22 #3 on the bearing rod 211 are used as the first electrodes 22*a*. The first electrodes 22*a* include the electrode 22 #3 at the outermost end 2111 of the bearing rod 211, and thus has the advantage of good attachment.

Preferably, each of the bearing rods 211 has two first electrodes 22*a*. Therefore, in this method, twelve first electrodes 22*a* are provided in total, which can form six mapping electrode pairs. The increase in number can greatly improve the scope and efficiency of collection of the electrophysiological signals, thus making the mapping more accurate. When the whole support frame 21 is attached to the target ablation area, electrocardic conduction signals in multiple directions can be collected, making the collected potential signals more accurate and avoiding the omission of a potential signal conducting in a direction perpendicular to the recording direction.

Third method: Two-adjacent first electrodes 22*a* are included in a plurality of electrodes 22 arranged on at least one bearing rod 211.

In this method, when the connector 3 is connected to the external mapping device, any two first electrodes 22*a* form a mapping electrode pair for mapping. Preferably, two first electrodes 22*a* on the same bearing rod 211 are used as a mapping electrode pair for mapping. However, in other embodiments, two first electrodes 22*a* on different bearing rods 211 may be used as a mapping electrode pair.

Correspondingly, in this embodiment, the electrode 22 is arranged in such a manner that the electrode 22 #1 and the electrode 22 #2 on the bearing rod 211 are used as the first electrodes 22*a*, or the electrode 22 #2 and the electrode 22 #3 on the bearing rod 211 are used as the first electrodes 22*a*.

Preferably, the electrode 22 #2 and the electrode 22 #3 are used as the first electrodes 22*a*. The first electrodes 22*a* include the electrode 22 #3 at the outermost end 2111 of the bearing rod 211, and thus has the advantage of good attachment.

In this method, preferably each of the bearing rods 211 is provided with two first electrodes 22*a*. Twelve first electrodes 22*a* are provided in total, which can form six mapping electrode pairs. The increase in number can improve the accuracy of mapping.

Over the radial dimension change of the support frame 21, the distance between two adjacent first electrodes 22*a* is constantly small, the far-field interference is also constantly small, and the electric field interference is small in this method, so the mapping accuracy is high.

Forth method: Three or more electrodes 22 on at least one bearing rod 211 are all the first electrodes 22*a*.

In this method, when the connector 3 is connected to the external mapping device, any two first electrodes 22*a* form a mapping electrode pair for mapping.

In this embodiment, preferably, the electrodes 22 on all the bearing rods 211 are all the first electrodes 22*a*. Accordingly, the ablation device has eighteen first electrodes 22*a*. The increase in number can effectively improve the accuracy of mapping.

In the methods listed above, different mapping methods can be formed by setting different first electrodes 22*a*. Each first electrode 22*a* and a corresponding first terminal 32*a* in the connector 3 can be electrically connected in a one-to-one correspondence mode as shown in the embodiment in FIG. 1*a*. The schematic views of specific connections in various methods are omitted here.

Figure 1D:
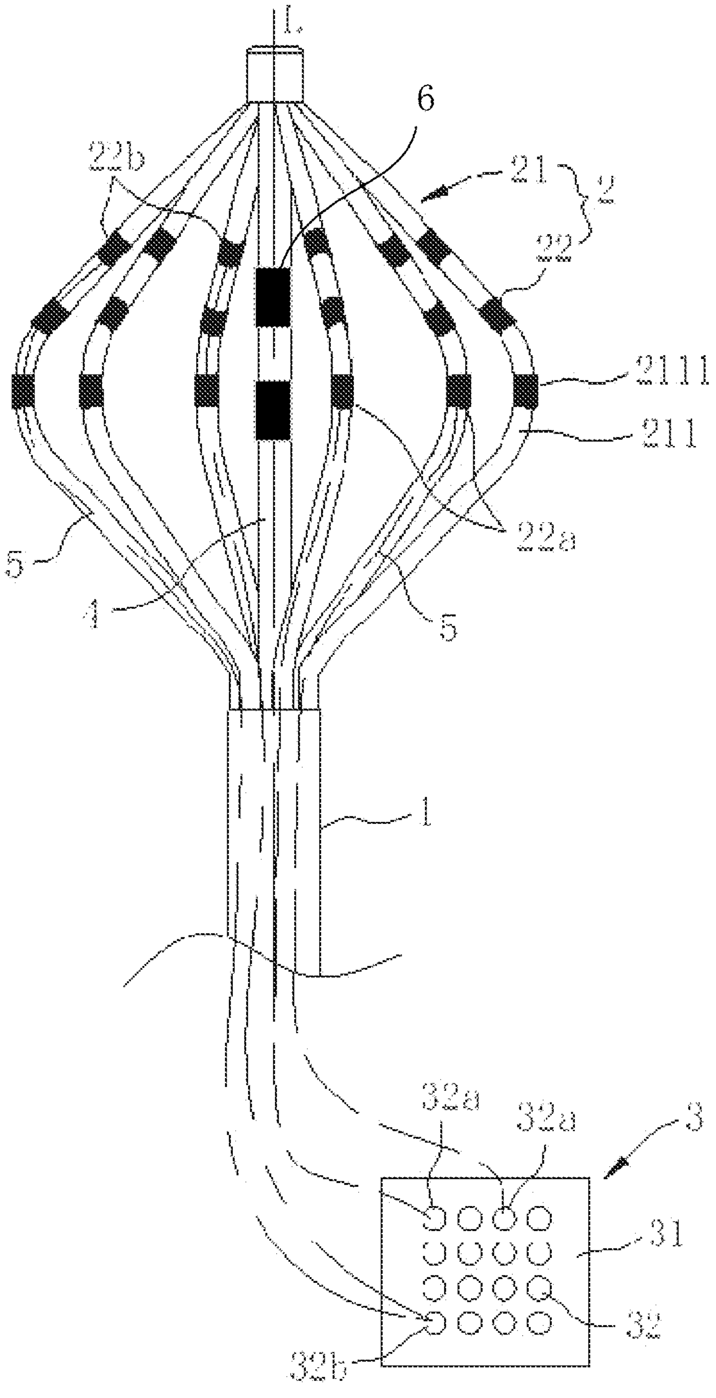
Figure 1E:
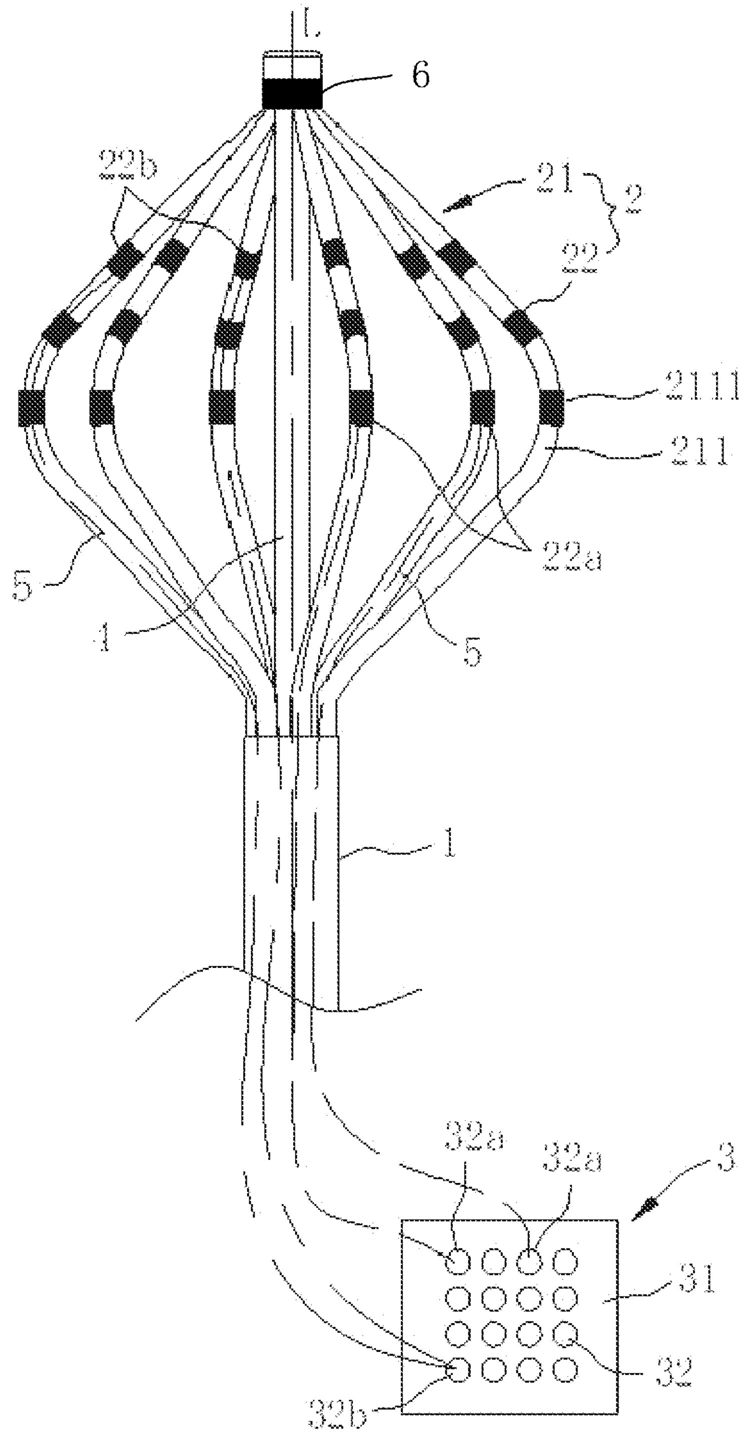

In the methods listed above, in other embodiments, as shown in FIG. 1*d*, the ablation device may further include a reference electrode 6. Each reference electrode 6 is electrically connected to one of the conductive terminals 32 in the connector 3 in a one-to-one correspondence mode. The reference electrode 6 can be located on the outer tube 1 or the driving member 4, and the reference electrode 6 and the first electrode 22*a* form a mapping electrode pair. In some embodiments, as shown in FIG. 1*e*, the reference electrode 6 can also be arranged at a most distal end of the support frame 21, and the reference electrode 6 and the first electrode 22*a* on the bearing rod 211 form a mapping electrode pair. In some cases, the reference electrode can also be provided on the body surface, and the reference electrode and one first electrode 22*a* on the ablation device form a mapping electrode pair.

When the ablation device according to this embodiment is used, the support frame 21 of the ablation assembly 2 is received in the collapsed state in a sheath, the ablation assembly 2 is delivered by the sheath to an intended position in the human body, then the sheath is withdrawn, then the support frame 21 is released, the support frame 21 is attached to a target ablation area, the connector 3 is connected to the external mapping device at this time, and the first electrode 22*a* implements the mapping with the aid of the first terminal 32*a*. After the mapping is completed, the connector 3 is switched to connect to the external ablation energy source, the ablation energy is transferred by the conductive terminal 32 to the electrode 22, and the electrode 22 ablates the target ablation area by pulsed-field ablation or by ablation in other energy forms. After the ablation, the connector 3 is switched to connect to the external mapping device, and the first electrode 22*a* is used for mapping again. It can be understood that the mapping and ablation can be carried out alternately according to the actual situation.

In addition, for a structure with the driving member 4 in this embodiment, the driving member 4 can be manipulated to adjust the degree of expansion of the support frame 21, so as to be well attached to the human tissue.

SECOND EMBODIMENT

Figure 2:
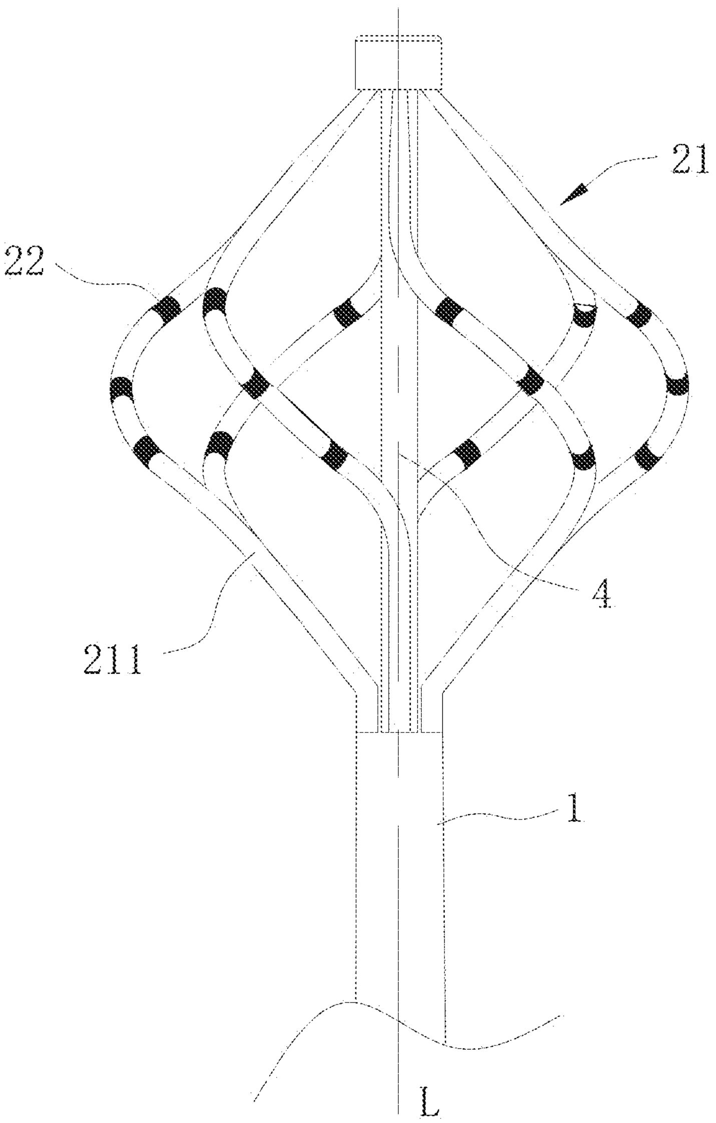
FIG. 2 is a schematic view of an ablation device according to a second embodiment of the present invention.
Figure 3:
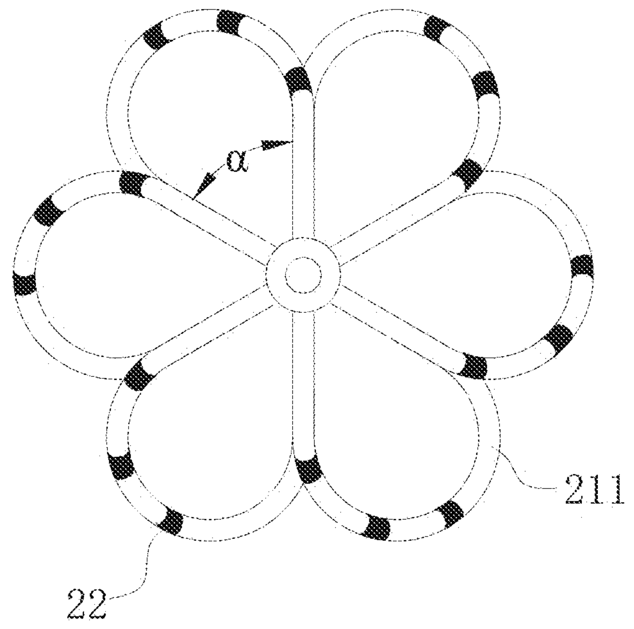
FIG. 3 is a top view of FIG. 2.
Figure 4:
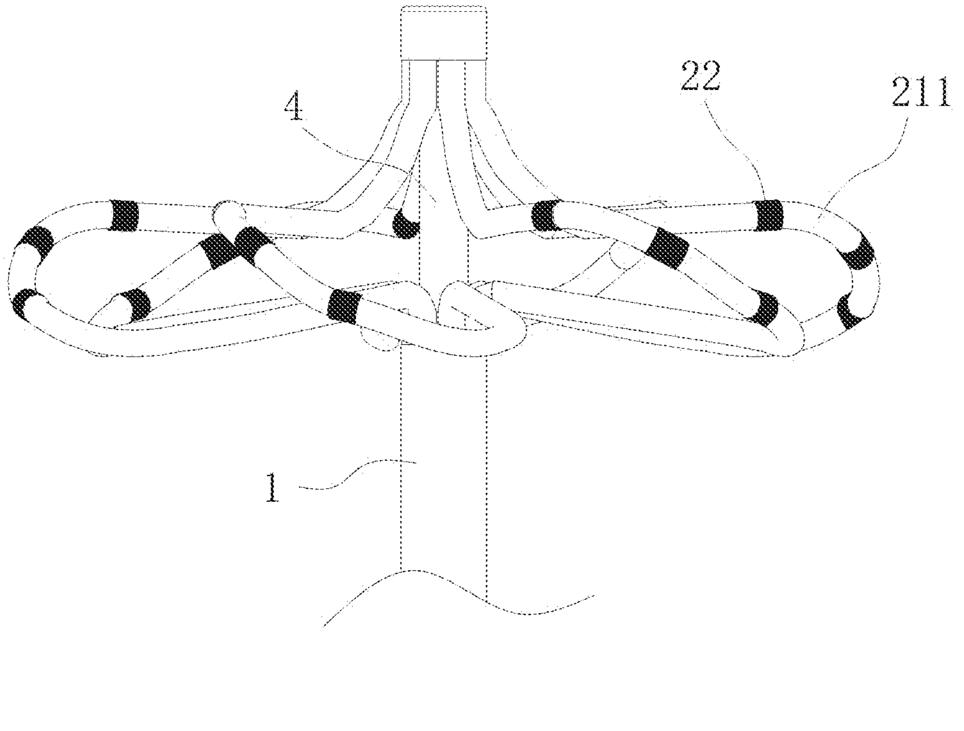
FIG. 4 is a schematic view showing a support frame in FIG. 2, in which the support frame is deformed by axially compression.

An ablation device according to this embodiment has the following differences from that in the first embodiment. Referring to FIGS. 2 to 4, in this embodiment, the bearing rod 211 of the support frame 21 helically extends from the proximal end to the distal end.

The helical shape of the bearing rod 211 can be formed by cutting and heat setting, or by other feasible technical means.

The proximal end of the bearing rod 211 is deflected from its distal end deflected by a preset angle α in the circumferential direction. Preferably, the preset angle α ranges from 30 degrees to 70 degrees.

The helical angle (i.e., the angle of twist) of the bearing rod 211 at different positions may be different. Particularly, the bearing rod 211 has an intermediate position between its proximal end and distal end, and the helical angle of the bearing rod 211 at the intermediate position is greater than the helical angle at its proximal end or distal end. That is, the bearing rod 211 does or does not deflect circumferentially at a small angle at its proximal end and distal end while extending in the axial direction, but the bearing rod 211 deflects circumferentially at a large angle at the intermediate position while extending in the axial direction. Preferably, the helical angle of the bearing rod 211 gradually decreases from the intermediate position to the proximal end of the bearing rod 211 or the distal end of the bearing rod 211.

It is to be understood that the intermediate position refers to a non-end position of the bearing rod 211, and may not particularly refer to a specific position.

In a preferred embodiment, the helical angles of the bearing rod 211 at various positions are symmetrically distributed on both sides of the intermediate position. When viewed from a direction shown in FIG. 3, the projection of the bearing rod 211 on a plane perpendicular to the axis L of the outer tube 1 is symmetrical. As shown in FIG. 3, the projection of the bearing rod 211 has a shape that is roughly defined by two straight line segments with an included angle α and an arc connected between the two straight line segments. In other embodiments (not shown), the projection of the bearing rod 211 may further have a shape that is an ellipse, an arc or other symmetrical geometric shapes.

The plurality of bearing rods 211 of the support frame 21 are evenly distributed at the circumferential position of the driving member 4. The projections of two adjacent bearing rods 211 on a plane perpendicular to the axis L of the outer tube 1 may partially overlap or not overlap at all.

In this embodiment, the helically extending structure of the bearing rod 211 can have a longer length of attachment to the target ablation area in the circumferential direction, so that the ablation assembly 2 has better conformity, and can be closely attached to the target ablation area.

Each bearing rod 211 is provided with a plurality of electrodes 22 spaced apart from each other along the axial direction. For the plurality of bearing rods 211, the plurality of electrodes 22 correspond one-to-one in the axial direction and are arranged at intervals in the circumferential direction around the axis L of the outer tube 1.

Each electrode 22 can be used as an ablation electrode or as a mapping electrode by being connected to the first terminal 32*a* of the connector 3 in a one-to-one correspondence mode. The connector 3 is not illustrated in the ablation device shown in FIGS. 2 to 4, and the mode of connection of the electrode 22 with the connector 3 can be made reference to the description in the first embodiment. In addition, the specific method for the electrode 22 to implement the ablation function and the mapping function can also be made reference to the description in the first embodiment, and will not be further described here.

THIRD EMBODIMENT

Figure 5:
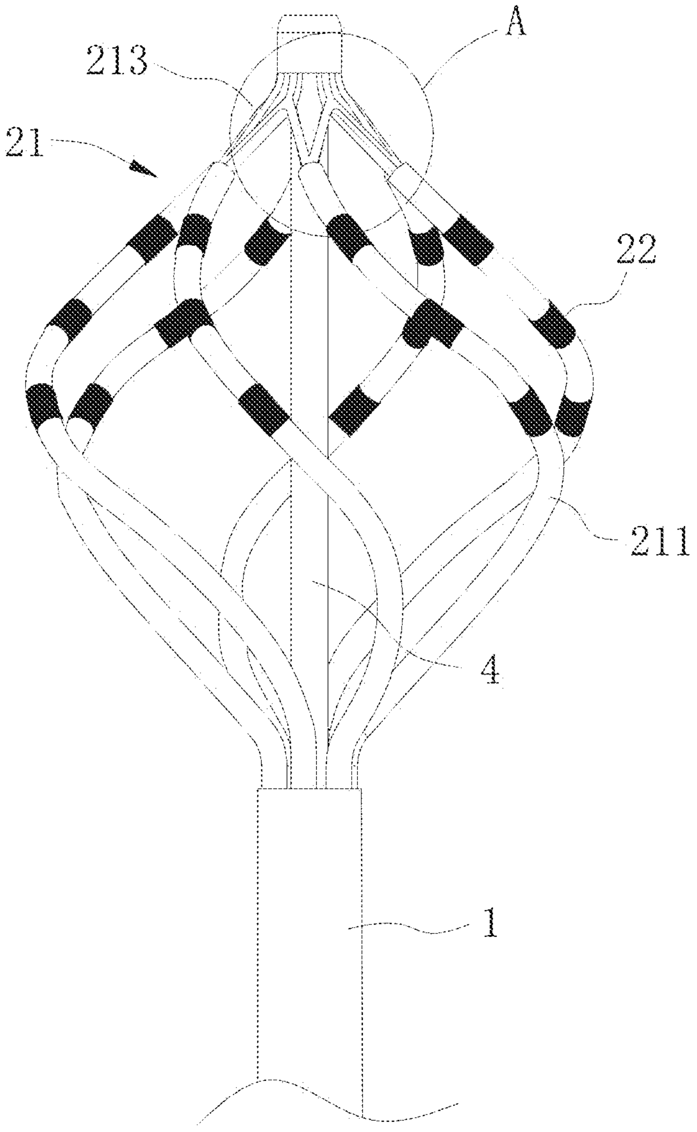
FIG. 5 is a schematic view of an ablation device according to a third embodiment of the present invention.
Figure 6:
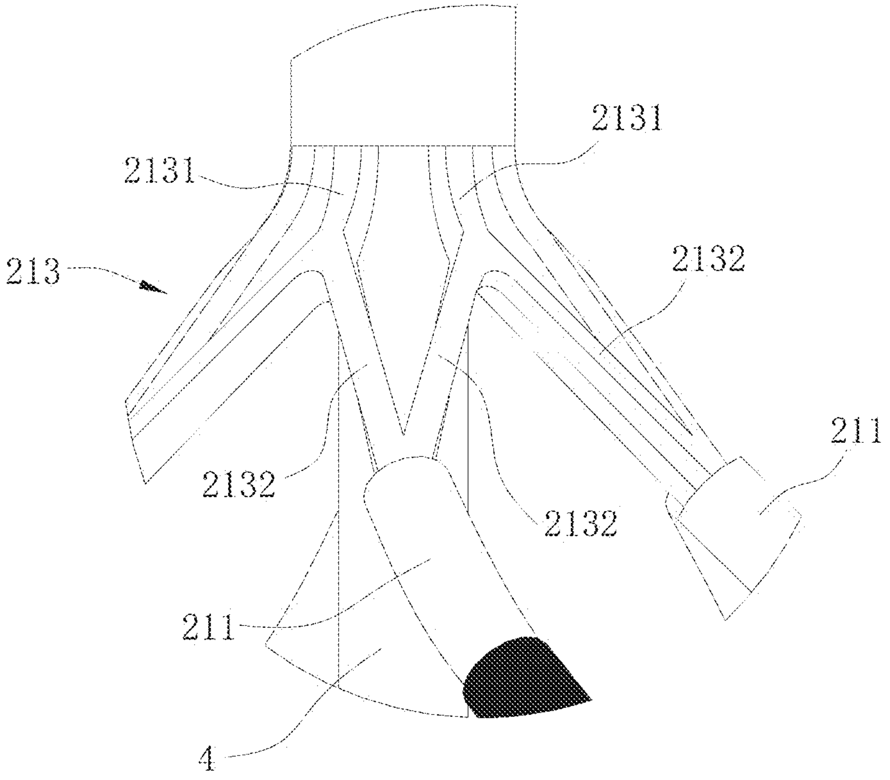
FIG. 6 is a partially enlarged view of part A in FIG. 5.
Figure 7:
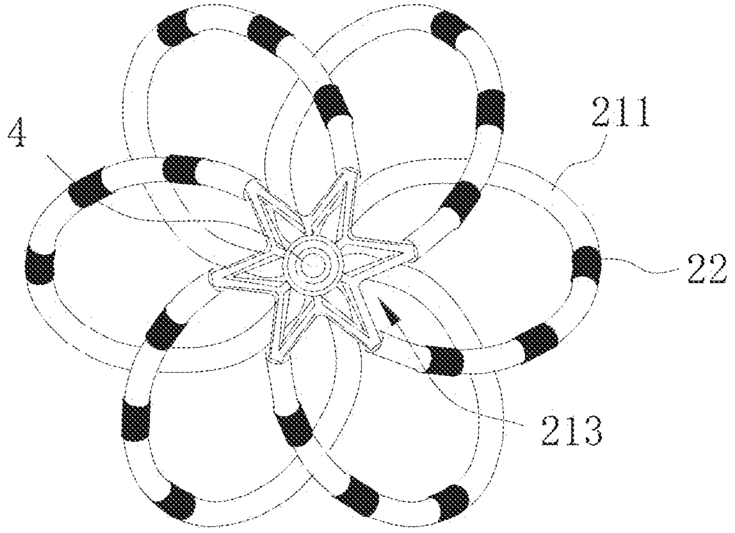
FIG. 7 is a top view of FIG. 5.

An ablation device according to this embodiment has the following differences from that in the first embodiment. Referring to FIGS. 5 to 7, in this embodiment, the support frame 21 further includes a locating frame 213. A proximal end of the locating frame 213 is connected to the distal ends of the plurality of bearing rods 211, and a distal end of the locating frame 213 is connected to the distal end of the driving member 4. When the support frame 21 is fully expanded, the radial dimension of the locating frame 213 is smaller than the radial dimension of a frame body defined by the plurality of bearing rods 211. The locating frame 213 and the plurality of bearing rods 211 can be formed by integrally cutting and shaping a nickel-titanium tube. The radial dimension of the locating frame 213 is the dimension of the locating frame 213 in a direction perpendicular to the axial direction of the driving member 4.

In the support frame 21, when the bearing rod 211 is applied with an external force perpendicular to its own axis or inclined to their own axis, the locating frame 213 can transfer the external force to another bearing rod 211 adjacent to the bearing rod 211 applied with the external force, whereby the adjacent bearing rod 211 is pulled. The bearing rod 211 has the performance of maintaining its own structure and state, so that an opposite force is formed on the adjacent bearing rod 211 to buffer or offset the force. The adjacent bearing rod 211 generates a reaction force perpendicular to the axis or inclined to the axis to confront the external force. In this way, the distance between the adjacent bearing rods 211 can be maintained, to keep the position of the bearing rod 211 stable, effectively maintain the stability of the relative positions of the electrodes 22 on the bearing rod 211, prevent the short-circuiting due to contact of the electrodes 22 with one another when the ablation device is working, effectively avoid the breakdown injury to tissues, and reduce the occurrence of serious adverse complications.

The locating frame 213 includes a plurality of main rods 2131 and a plurality of branch rods 2132. The plurality of main rods 2131 are arranged along the circumferential direction of the driving member 4. A distal end of each main rod 2131 is connected to the distal end of the driving member 4, and a proximal end of each main rod 2131 is connected to distal ends of a plurality of branch rods 2132. The distal end of each bearing rod 211 is connected to proximal ends of a plurality of corresponding branch rods 2132, and the distal ends of a plurality of branch rods 2132 connected to the same bearing rod 211 are connected to different main rods 2131. Different bearing rods 211 connected by the same main rod 2131 and the plurality of branch rod 2132 can be connected to each other by the corresponding main rod 2131 and the corresponding branch rods 2132, to distribute the stress on respective bearing rods 211. For example, the stress on a single bearing rod 211 can be distributed onto other bearing rods 211 connected to the corresponding main rod 2131.

The plurality of branch rods 2132 connected to the same main rod 2131 have an angle therebetween, so that they can be connected to a plurality of bearing rods 211 or other branch rods 2132 respectively.

In this embodiment, it is preferable that the proximal end of each main rod 2131 is connected with the distal ends of two branch rods 213, the two branch rods 2132 connected to the same main rod 2131 extend in directions away from each other, and the proximal ends of the two branch rods 2132 connected to the same main rod 2131 are connected to the distal ends of two adjacent bearing rods 211. Accordingly, the external force applied on a single bearing rod 211 is transmitted to two adjacent bearing rods 211 through the branch rods 2132. Moreover, when the relative position between the driving member 4 and the outer tube 1 is adjusted to drive the support frame 21 to contract or expand, because two adjacent main rods 2131 are constrained by two branch rods 2132 bound together, the branch rods 2132 pull the main rods 2131 in the axial direction and the radial direction, so that the deformation of the main rods 2131 in the radial direction and the axial direction is not too large. This is beneficial to the maintenance of the locating frame 213 in the shape of a mesh basket, such that when the radial dimension of the support frame 21 is changed, the ablation device can maintain a good centering effect, and the ablation device can be accurately directed to the periphery of the pulmonary vein ostium when the ablation device is used for circular ablation at the pulmonary vein ostium.

In this embodiment, the plurality of branch rods 2132 are connected end to end to form a wave-shaped ring structure surrounding the driving member 4, the proximal end of each main rod 2131 is connected to the peak of the wave-shaped ring structure, and the distal end of each bearing rod 211 is connected to the valley of the wave-shaped ring structure. Therefore, the external force applied onto the bearing rod 211 can be transmitted through the wave-shaped ring structure defined by these branch rods 2132.

Preferably, the joint of the main rod 2131 and the branch rod 2132 is bent towards a side away from the driving member 4, and the joint of the bearing rod 211 and the branch rod 2132 is bent towards a side approaching the driving member 4.

In this embodiment, the arrangement of the electrode 22 and the specific method for the electrode 22 to implement the ablation and mapping function can be made reference to the description in the first embodiment, will not be repeated here.

FOURTH EMBODIMENT

Figure 8:
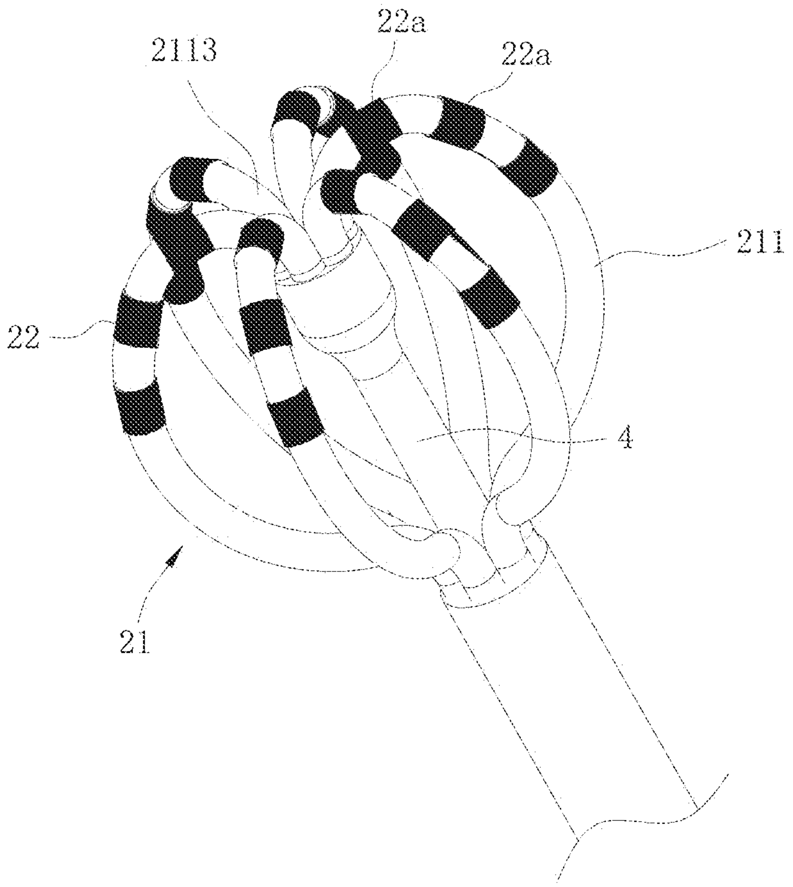
FIG. 8 is a schematic view of an ablation device according to a fourth embodiment of the present invention.

An ablation device according to this embodiment has the following differences from that in the first embodiment. Referring to FIG. 8, in this embodiment, the distal end of the bearing rod 211 is formed with a backward enclosure portion 2113. The backward enclosure portion 2113 is formed by bending the most distal end of the bearing rod 211 towards the axis of the driving member 4 and extending towards the proximal end. The backward enclosure portion 2113 is connected to the distal end of the driving member 4, and the most distal end of the bearing rod 211 exceeds the distal end of the driving member 4 in the distal direction. The backward enclosure portion 2113 defined by the plurality of bearing rods 211 are each connected to the distal end of the driving member 4, and the contour of the support frame 21 is roughly in the shape of a spherical or cage structure.

Due to the differences in the special structures and anatomical characteristics of mitral isthmus, cavotricuspid isthmus, and left atrium apex, and the influence of physiological activities in the heart environment, the ablation treatment at these sites puts forward higher requirements for stable attachment and ablation. The design of the support frame 21 in this embodiment has the following advantages. On one hand, because the overall shape of the support frame 21 is spherical or cage-like, the arc-shaped or spherical structure on the surface of the spherical or cage-like support frame 21 facilitates the attachment and ablation. Accordingly, the support frame 21 can be easily attached to and positioned in the target ablation area at any angle. In this manner, the ablation device can be used for dot-and-dash ablation or circular ablation, dot-and-dash ablation at the left atrium apex, mitral isthmus, and tricuspid isthmus, or circular ablation at the pulmonary vein ostium. On the other hand, the structural design of the backward enclosure portion 2113 enables the distal end of the driving member 4 to locate inside the axial contour of the bearing rod 211, so as to avoid the damage to the atrial tissue caused by a tip formed by the protrusion of the distal end of the driving member 4, and well conform to the ablation area in the heart.

The length of the backward enclosure portion 2113 can be set as required, and thus the shape of the distal end of the support frame 21 can be changed, to adapt to different target ablation areas. When the driving member 4 has a tubular structure, the backward enclosure portion 2113 can be clamped in the tubular structure of the driving member 4.

Each bearing rod 211 is provided with a plurality of electrodes 22 spaced apart from each other along the axial direction. At least one bearing rod 211 is provided with the electrode 22 at its most distal end, whereby the support frame 21 is provided with the electrode 22 at its most distal end, so that the ablation device can perform local ablation.

Preferably, the most distal end of each bearing rod 211 is provided with the electrode 22. Preferably, the electrode 22 at the most distal end and the electrode 22 adjacent to the electrode 22 at the most distal end of each bearing rod 211 are set as the first electrodes 22*a*, and the first electrodes 22*a* can be used for both ablation and mapping.

The specific method for the electrode 22 to implement the ablation function and the mapping function can also be made reference to the description in the first embodiment, and will not be repeated here.

FIFTH EMBODIMENT

Figure 9:
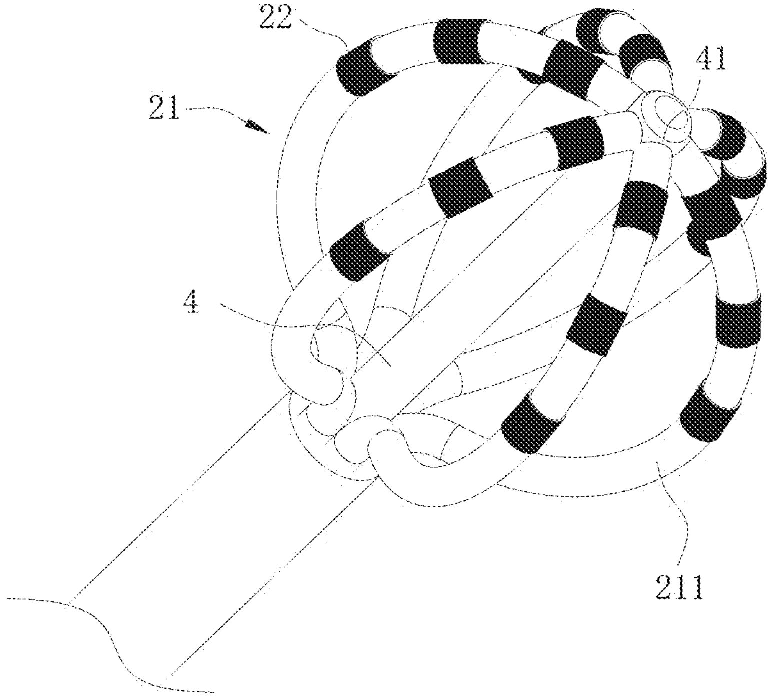
FIG. 9 is a schematic view of an ablation device according to a fifth embodiment of the present invention.

An ablation device according to this embodiment has the following differences from that in the first embodiment. Referring to FIG. 9, in this embodiment, the distal end of each bearing rod 211 of the support frame 21 is connected to the outer periphery of the driving member 4, and the tangent line of the distal end of each bearing rod 211 is perpendicular to the axis of the driving member 4, so that the distal ends of the plurality of bearing rods 211 are bound together to form a shape with an arc or round structure.

Particularly, the outer periphery of the driving member 4 is provided with a plurality of insertion holes 41, and each insertion hole 41 is correspondingly inserted with the distal end of one bearing rod 211, such that each bearing rod 211 is connected into each insertion hole 41 in a one-to-one correspondence mode. The end of the bearing rod 211 connected to the driving member 4 is the most distal end of the bearing rod 211, and the most distal end of the driving member 4 is flatly smoothly or circularly smoothly connected with the most distal ends of the bearing rods 211.

In this structure, the distal end of the ablation device also has no protruding tip, to avoid the damage to the atrial tissue and well conform to the ablation area in the heart.

In this embodiment, the arrangement of the electrode 22 and the specific method for the electrode 22 to implement the ablation and mapping function can be made reference to the sescription in the first embodiment, will not be repeated here.

SIXTH EMBODIMENT

Figure 10:
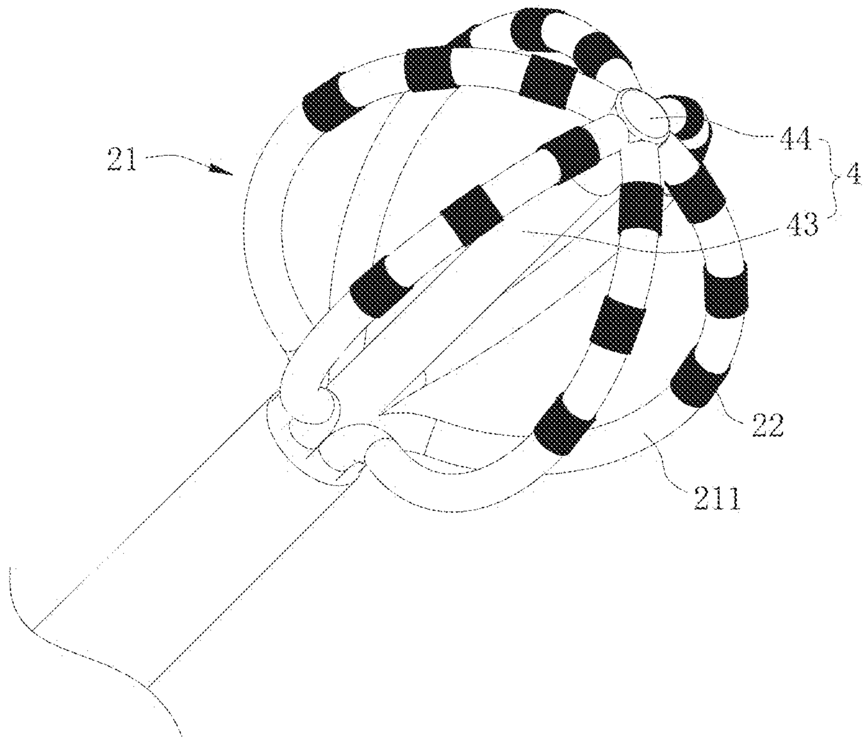
FIG. 10 is a schematic view of an ablation device according to a sixth embodiment of the present invention.

An ablation device according to this embodiment has the following differences from that in the fifth embodiment. Referring to FIG. 10, the driving member 4 includes a driving rod 43 and a joint 44 arranged at the distal end of the driving rod 43. The bearing rods 211 are each connected to the outer periphery of the joint 4, the tangent line of the distal end of bearing rod 211 is substantially perpendicular to the axis of the joint 44, and a distal end of the joint 44 is approximately tangent to or forms a relatively circularly smooth transition with the distal ends of the plurality of bearing rods 211.

A distal end surface of the joint 44 and a distal end surface of the support frame 21 are roughly on the same tangent plane, and the contour of the support frame 21 is roughly of a spherical or cage-like shape. Therefore, the support frame 21 can be attached stably as a whole, makes the ablation feasible at any angle, and is well applicable to the dot-and-dash ablation of the atrial wall, the mitral isthmus, and the tricuspid isthmus, to achieve the goal of rapid, efficient and high-quality ablation in the whole process.

The joint 44 can be used as an electrode with mapping and ablation performance, such as an ablation electrode or a mapping electrode, so as to fully improve the usability of the joint 44, and systematically enhance the usability of the ablation device. When the joint 44 is used as an ablation electrode, since the distal end surface of the joint 44 is approximately tangent to or form a relatively circularly smooth transition with the distal ends of the plurality of bearing rods 211, the joint 44 and the electrodes 22 arranged at the distal ends of the plurality of bearing rods 211 can be located on the same ablation spherical surface or ablation cambered surface, to achieve the goal of rapid, efficient and high-quality ablation in the whole process. Further, when the joint 44 is used as an ablation electrode, it can be used for ablation by radiofrequency ablation or for ablation by pulsed-field ablation. Adjustments can be made by an operator by making a targeted ablation strategy according to different conditions of different patients, to expand the scope of ablation at the lesion position, and meet the ablation requirements of more indications. When the joint 44 is used as a mapping electrode, the joint 44 can be solely connected to one conductive terminal 32 of the connector (not shown) by a wire in a one-to-one correspondence mode. The connector 44 can be well attached to the surface of the myocardium, which is beneficial to improving the mapping accuracy. The joint 44 can be used as a mapping electrode alone. Moreover, the joint 44 can also form a mapping electrode pair with the first electrode 22*a* on the bearing rod 211.

In this embodiment, the arrangement method of the electrode 22 on the bearing rod 211 and the specific method for the electrode 22 to implement the ablation function and the mapping function can also be made reference to the description in the first embodiment, which will not be repeated here.

SEVENTH EMBODIMENT

Figure 11:
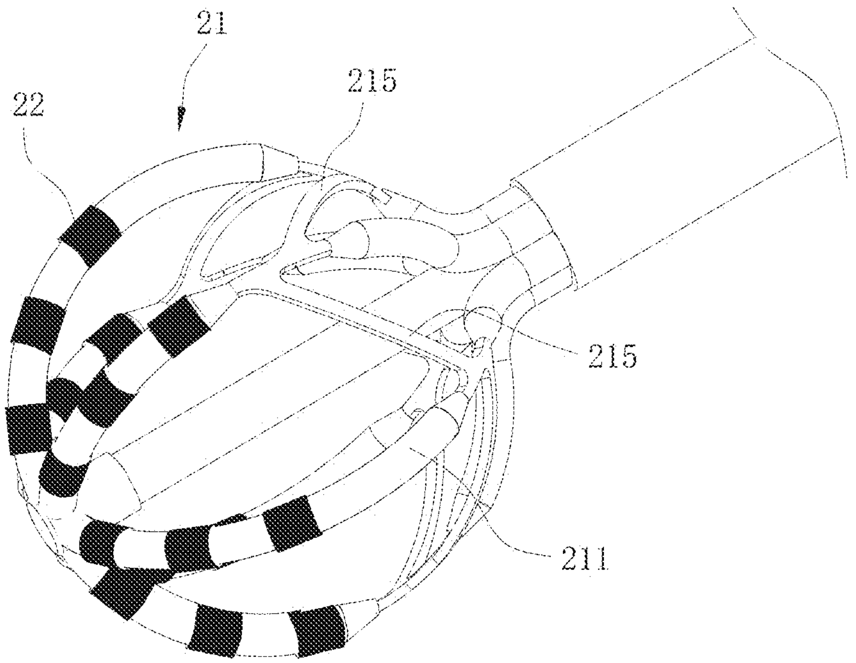
FIG. 11 is a schematic view of an ablation device according to a seventh embodiment of the present invention.

An ablation device according to this embodiment has the following differences from that in the sixth embodiment. Referring to FIG. 11, in this embodiment, the support frame 21 further includes a plurality of support rods 215, and each of the support rods 215 is used for connecting two adjacent bearing rods 211. One end of each support rod 215 is connected to one of the bearing rods 211, and the other end is connected to another adjacent bearing rod 211. The support rod 215 extends obliquely, and two ends of the support rod 215 are spaced in the axial direction of the outer tube 1.

The support rod 215 can restrain the adjacent bearing rods 211. In this way, the distance between the adjacent bearing rods 211 can be maintained, to prevent the bearing rod 211 from shift when the ablation device works, and avoid short-circuiting due to contact of the electrodes 22 on adjacent bearing rods 211 with one another, thus avoiding the occurrence of arcing.

Moreover, the support rods 215 improve the uniformity in distribution of the bearing rods 211 in the circumferential direction, making it impossible for the support frame 21 to twist and deform as a whole, and improving the accuracy and efficiency of ablation and mapping of the ablation device.

In this embodiment, one support rod 215 is provided at either side of the same bearing rod 211, and the support rods 215 provided at two side of the same bearing rod 211 both extend distally or proximally to connect another adjacent bearing rods 211 respectively. That is, the two support rods 215 provided at two sides of the same bearing rod 211 extend away from each other.

In this embodiment, the support rods 215 at two sides of the same bearing rod 211 are asymmetrical with respect to the bearing rod 211, that is, the individual support rods 215 at two sides of the bearing rod 211 are connected to the bearing rod 211 at positions that are axially spaced. First ends of the two support rods 215 are connected to different positions on the same bearing rod 211, and second ends extend in directions away from each other. Such an asymmetric structure is beneficial to improving the stable attachment of the whole spherical structure of the support frame 21, the controllability of the arc shape of the spherical structure, and the stability of the whole spherical structure, so that the spherical frame is not prone to deformation.

It is to be understood that the position of the support rod 215 is not limited. The support rod 215 can be arranged at a middle position of the bearing rod 211, at a distal position of the bearing rod 211, or at a proximal position of the bearing rod 211.

In this embodiment, the arrangement method of the electrode 22 on the bearing rod 211 and the specific method for the electrode 22 to implement the ablation function and the mapping function can also be made reference to the description in the first embodiment, which will not be repeated here.

EIGHTH EMBODIMENT

Figure 12:
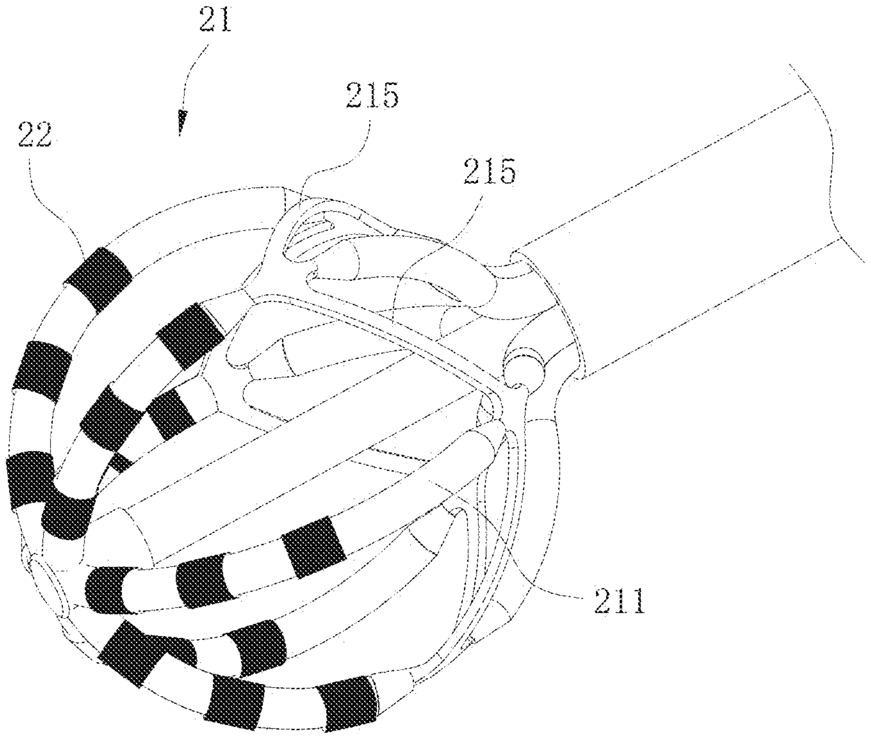
FIG. 12 is a schematic view of an ablation device according to an eighth embodiment of the present invention.

An ablation device according to this embodiment has the following differences from that in the seventh embodiment. Referring to FIG. 12, in this embodiment, the support rods 215 at two sides of the same bearing rod 211 are arranged symmetrically with respect to the bearing rod 211.

In this structure, as observed from the whole outer periphery of the support frame 21, the support rods 215 arranged between any two bearing rods 211 in the plurality of bearing rods 211 form a ring structure of substantially continuous V shapes or W shapes. The ring structure enables the plurality of support rods 215 to support and abut against one other, thereby constraining each bearing rod 211 in the axial direction and the circumferential direction, and improving the stability of the shape of the support frame 21. This is beneficial to improving the accuracy of ablation and mapping.

In this embodiment, the arrangement method of the electrode 22 on the bearing rod 211 and the specific method for the electrode 22 to implement the ablation function and the mapping function can also be made reference to the description in the first embodiment, which will not be repeated here.

Although the present invention has been described with reference to several exemplary embodiments, it should be understood that the terminology used is illustrative and exemplary rather than limiting. Since the present invention can be implemented in various forms without departing from the spirit or essence of the present invention, it should be understood that the above-mentioned embodiments are not limited to any of the foregoing details, but should be broadly interpreted within the spirit and scope defined by the appended claims. Therefore, all changes and modifications that fall within the scope of the claims or their equivalents are intended to be covered by the appended claims.

The invention claimed is:

1. An ablation device, comprising:

an outer tube;

an ablation assembly, provided at a distal end of the outer tube and comprising a support frame which is radially collapsible and expandable and a plurality of electrodes arranged on the support frame, wherein the plurality of electrodes comprises at least one first electrode for mapping; and a connector, provided at a proximal end of the outer tube, wherein the connector comprises a plurality of conductive terminals, the connector is electrically connected to the plurality of electrodes through the plurality of conductive terminals, the plurality of conductive terminals comprises at least one first terminal, wherein a number of the at least one first electrode is equal to a number of the at least one first terminal, and each of the at least one first terminal is electrically connected to one corresponding first electrode in a one-to-one correspondence manner, so that when the connector is connected to an external mapping device, the at least one first electrode implements mapping through the first terminal, wherein the support frame comprises a plurality of bearing rods arranged circumferentially around an axis of the outer tube, proximal ends of the plurality of bearing rods are connected to the distal end of the outer tube, and distal ends of the plurality of bearing rods are converged towards the axis of the outer tube; and wherein the plurality of electrodes are provided on at least a portion of the plurality of bearing rods;

wherein the ablation device further comprises a driving member, wherein the driving member is arranged in the outer tube, a distal end of the driving member is connected to the distal ends of the plurality of bearing rods, and the driving member is axially movable relative to the outer tube to drive the support frame to radially collapse or radially expand; and wherein the support frame further comprises a locating frame, wherein the locating frame comprises a plurality of main rods and a plurality of branch rods; the plurality of main rods are arranged along the circumferential direction of the driving member, a distal end of each main rod is connected to the distal end of the driving member, and a proximal end of each main rod is connected to distal ends of a plurality of branch rods; and the distal end of each bearing rod is connected to proximal ends of a plurality of corresponding branch rods, and the distal ends of a plurality of branch rods connected to a same bearing rod are connected to different main rods.

2. The ablation device according to claim 1, wherein the at least one first electrode comprises a plurality of first electrodes, each of at least two of the plurality of bearing rods is provided with one first electrode of the plurality of first electrodes such that at least two first electrodes are respectively provided on the at least two of the plurality of bearing rods; and when the connector is connected to the external mapping device, any two of the at least two first electrodes respectively provided on the at least two of the plurality of bearing rods are used as a mapping electrode pair for mapping.

3. The ablation device according to claim 2, wherein each of the plurality of bearing rods is provided with one first electrode, the plurality of first electrodes on the plurality of bearing rods correspond in the axial direction and are arranged at intervals in the circumferential direction around the axis of the outer tube.

4. The ablation device according to claim 3, wherein each first electrode is located at a position on the corresponding bearing rod that is farthest from the axis of the outer tube in the radial direction.

5. The ablation device according to claim 4, wherein when the connector is connected to the external mapping device, the first electrodes on two adjacent bearing rods are used as a mapping electrode pair for mapping.

6. The ablation device according to claim 1, wherein at least one of the plurality of bearing rods is provided with three or more electrodes at intervals in the axial direction, and the three or more electrodes comprise at least two first electrodes; and when the connector is connected to the external mapping device, any two of the first electrodes are used as a mapping electrode pair for mapping.

7. The ablation device according to claim 6, wherein one of the first electrodes is located at a position on the corresponding bearing rod that is farthest from the axis of the outer tube.

8. The ablation device according to claim 6, wherein each of the plurality of bearing rods is provided with three or more electrodes at intervals in an extending direction, and for the plurality of bearing rods, the three or more electrodes correspond one-to-one in the axial direction and are arranged at intervals in the circumferential direction around the axis of the outer tube.

9. The ablation device according to claim 1, wherein the plurality of electrodes comprises a plurality of second electrodes for ablation only, the plurality of conductive terminals comprises at least one second terminal electrically connected to the plurality of second electrodes, and a number of the second terminal is less than or equal to a number of the second electrode.

10. The ablation device according to claim 1, wherein each bearing rod has an outermost end that is farthest from the axis of the outer tube in a radial direction, and each electrodes provided on one corresponding bearing rod is arranged between the distal end and the outermost end of the corresponding bearing rod.

11. The ablation device according to claim 1, wherein each bearing rod helically extends from the proximal end to the distal end, and the distal end of each bearing rod has a circumferential deflection angle relative to the proximal end of a same bearing rod in the circumferential direction of the outer tube.

12. The ablation device according to claim 11, wherein each bearing rod has an intermediate position between the proximal end and the distal end of the bearing rod, and a helical angle of each bearing rod at the intermediate position is greater than the helical angle of the same bearing rod at the proximal end or distal end.

13. The ablation device according to claim 11, wherein a proximal end of the locating frame is connected to the distal ends of the plurality of bearing rods, and a distal end of the locating frame is connected to the distal end of the driving member; and when the support frame is fully expanded, a radial dimension of the locating frame is smaller than a radial dimension of a frame body defined by the plurality of bearing rods.

14. The ablation device according to claim 1, wherein a projection of each bearing rod on a plane perpendicular to the axis of the outer tube is symmetrical.

15. The ablation device according to claim 1, wherein the proximal end of each main rod is connected to the distal ends of two branch rods, the two branch rods connected to the same main rod extend in directions away from each other, and the proximal ends of the two branch rods connected to the same main rod are connected to the distal ends of two adjacent bearing rods.

16. The ablation device according to claim 1, wherein the distal end of the bearing rod is formed with a backward enclosure portion, the backward enclosure portion is formed by bending the most distal end of each bearing rod towards an axis of the driving member and extending towards the proximal end, the backward enclosure portion is connected to the distal end of the driving member, and a most distal end of each bearing rod exceeds the distal end of the driving member in a distal direction.

17. The ablation device according to claim 16, wherein the support frame further comprises a plurality of support rods, one end of each support rod is connected to one of the plurality of bearing rods, and another end of each support rod is connected to another adjacent bearing rod.

18. The ablation device according to claim 1, wherein the distal end of each bearing rod is connected to an outer periphery of the driving member, and a tangent line of the distal end of each bearing rod is perpendicular to the axis of the driving member.

19. The ablation device according to claim 1, wherein when the connector is connected to the external ablation energy source, the at least one first electrode is independently controllable by the at least one first terminal to discharge, so that the at least one first electrode controlled to discharge transfers ablation energy outputted by the external ablation energy source to an area where the at least one first electrode is located for local ablation.

* * * * *